United States Patent [19]

Jewusiak et al.

[11] 4,294,355

[45] Oct. 13, 1981

[54] CARTRIDGE FOR HEMOSTATIC CLIPS

[75] Inventors: Stephen J. Jewusiak, Denville; Howard Beroff, Bridgewater; Michael Schuler, Edison, all of N.J.

[73] Assignee: Ethicon, Inc., Somerville, N.J.

[21] Appl. No.: 100,778

[22] Filed: Dec. 6, 1979

[51] Int. Cl.³ .............................................. B65D 85/24
[52] U.S. Cl. ................................... 206/339; 206/340; 206/804; 128/325
[58] Field of Search ............... 206/339, 340, 804, 228, 206/229, 334, 336, 337, 341, 348, 355; 128/325

[56] References Cited

U.S. PATENT DOCUMENTS 3,713,533  1/1973  Reimels ............................... 206/339
4,076,120  2/1978  Carroll et al. ........................ 206/339
4,146,130  3/1979  Samuels et al. ..................... 206/339

Primary Examiner—Joseph Man-Fu Moy
Attorney, Agent, or Firm—Robert L. Minier

[57] ABSTRACT

A cartridge for holding a plurality of plastic, snap-closure hemostatic clips in a manner which allows each clip to be individually loaded into a forceps-type clip applier. The cartridge consists of an elongated body having a stepped central rail on which open clips are positioned with the head of the clip resting on the step on one side of the rail, and the tail of the clip projecting into a space on the opposite side of the rail. Means are provided for retaining the clips in position on the rail until loaded into the clip applier.

22 Claims, 8 Drawing Figures

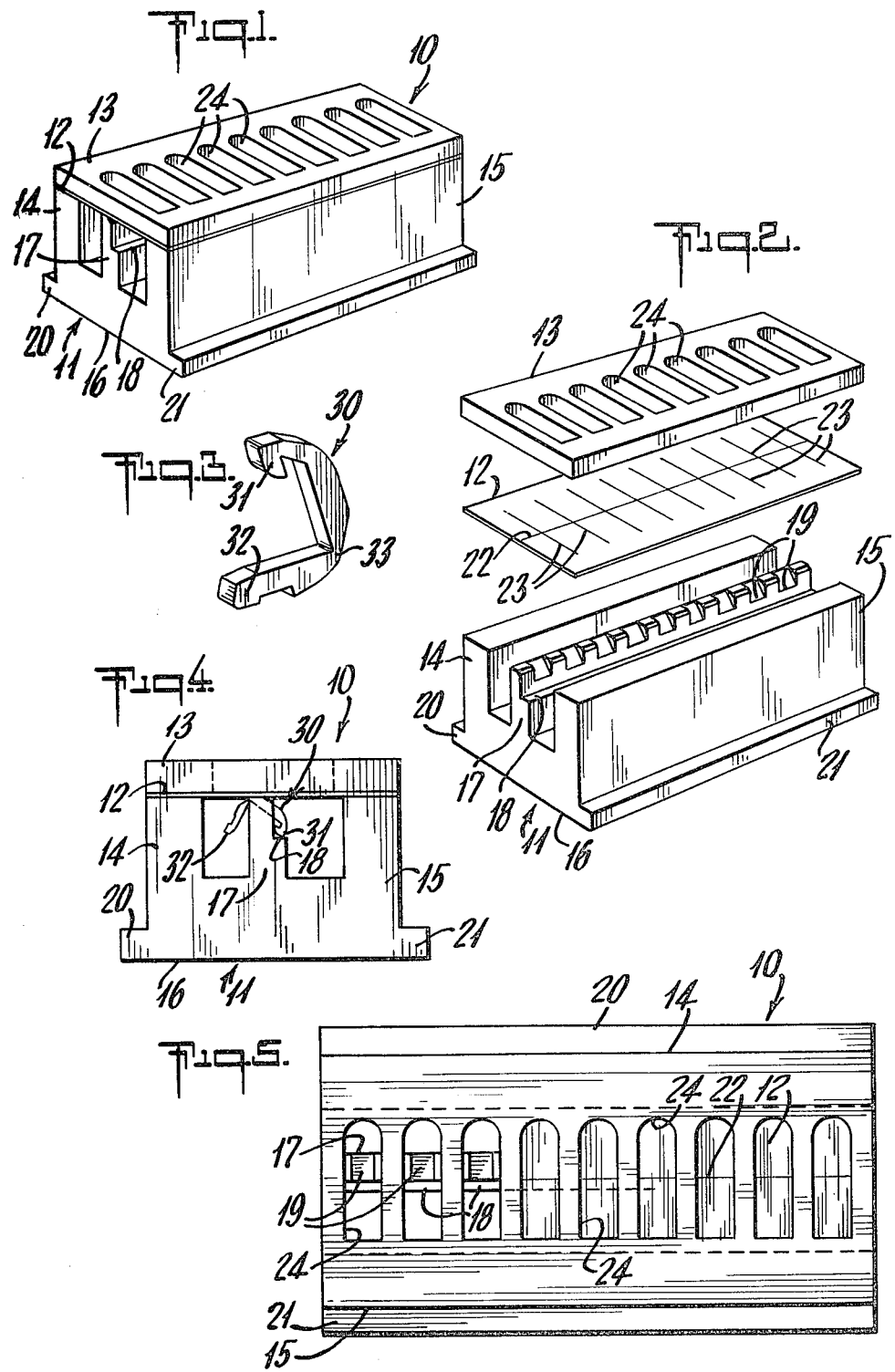

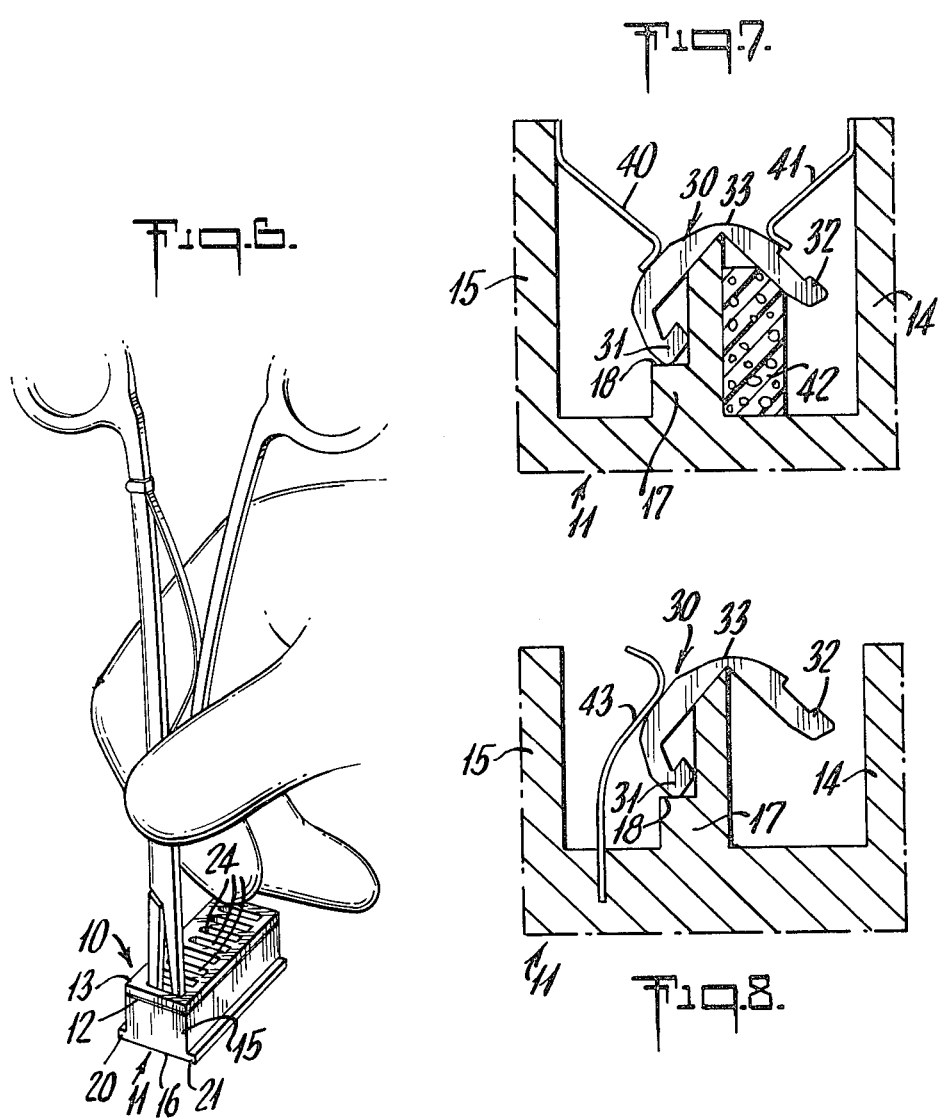

CARTRIDGE FOR HEMOSTATIC CLIPS

BACKGROUND OF THE INVENTION

This invention relates to a cartridge containing a plurality of hemostatic clips and, more particularly, to a cartridge for snap-closure-type plastic ligating clips.

Conventional ligating clips of the prior art have been fabricated of stainless steel or tantalum rectangular wire formed into a symmetrical V or U shape. Cartridges for such clips typically comprise an open, box-like structure with a corresponding V- or U-shaped center rail to support the clips in an inverted position. Various means have been provided to hold the clips on the rail until they are loaded into a forceps-type clip applier. Typical of such prior art clips and cartridges are those illustrated in U.S. Pat. Nos. 3,713,533; 4,076,120; and 4,146,130.

Recent work in the field of molded plastic ligating clips has resulted in a particularly useful clip design having an unsymmetrical configuration somewhat resembling that of a safety pin. One leg of the plastic clip is provided with a hook-like latching mechanism or head to receive and hold the end of the other leg of the clip when the clip is closed over the vessel being ligated. Because of the physical properties and unsymmetrical design of the plastic clip, cartridges of the type used for metallic clips were found to be unsuitable for use with the plastic clip. In particular, the plastic clips are required to be oriented in the holder and held in a manner which allows individual clips to be retrieved with the clip applier in the predetermined orientation. It is accordingly an object of the present invention to provide a cartridge for a plurality of plastic ligating clips. It is a further object of the invention to provide a cartridge which assures proper orientation of an unsymmetrical plastic clip within the cartridge. It is a yet further object in one embodiment of the present invention to provide a keyed access aperture communicating with each clip and oriented in accordance with the orientation of the clip within the cartridge. These and other objects of the present invention will be apparent from the ensuing description and claims.

SUMMARY

The ligating clip cartridge of the present invention comprises an open, channel-like body member having a base and two side walls and a central rail extending parallel to said side walls and vertically from the base of said body member. The rail is a compound rectangular member having a straight back wall and a stepped front wall to provide a ledge running the full length of the rail and a top section of reduced thickness relative to the bottom section. The top surface of the rail is notched at spaced intervals and at an angle extending from the upper edge of the rear wall downward toward the step on the front wall. The width and spacing of the notches correspond to the width and desired spacing of the plastic clips which are ultimately to be positioned thereon.

The plastic clips for use with the cartridge of the present invention are those of a safety-pin-type having a latching head at the end of one leg. The clips are mounted in the cartridge by placing each clip in a slot at the top of the rail with the head of the clip resting on the ledge of the rail, and the other leg of the clip extending freely into the space between the rail and the adjacent wall of the body member.

Means such as finger springs or a cover sheet are provided for holding the clips in position on the rail. An optional cover plate having a series of apertures sized to receive the nose of a clip-applying forceps, and spaced to communicate with the clips within the cartridge may be secured across the open side of the channel to complete the cartridge assembly. The apertures within the cover plate are preferably unsymmetrical and oriented in accordance with the orientation of the clips on the rail below.

DESCRIPTION OF THE DRAWINGS

The invention will be particularly described with reference to the following detailed description of the preferred embodiments of the present invention considered together with the attached drawings in which FIG. 1 is a view in perspective of one embodiment of an assembled cartridge formed in accordance with this invention.

FIG. 2 is an exploded view in perspective illustrating the elements and assemblage of the cartridge of FIG. 1.

FIG. 3 is a view in perspective of one embodiment of a plastic ligating clip useful in the cartridge of this invention.

FIG. 4 is an end plan view of the cartridge of FIG. 1 illustrating the placement of the clips in the cartridge.

FIG. 5 is a top plan view of the cartridge of FIG. 1 after some of the clips have been removed.

FIG. 6 is a view in perspective of a forceps-type clip applier inserted into the cartridge of FIG. 1 to remove a clip therefrom.

FIG. 7 is a cross-sectional end view of another embodiment of the cartridge of the present invention illustrating means by which the clip is held on the rail.

FIG. 8 is a cross-sectional end view of another cartridge of this invention illustrating means by which the clip may be held on the rail.

DESCRIPTION OF SPECIFIC EMBODIMENTS

With reference to FIGS. 1 and 2 there is illustrated as one embodiment of the present invention cartridge 10 comprising body member 11, film 12, and cover 13. Body 11 is an open channel having side walls 14 and 15 extending from base 16. Central rail 17 extends along the length of the channel parallel to walls 14 and 15, and at the approximate center of base 16. Rail 17 is stepped on the front side as illustrated to form ledge 18 extending the full length thereof. Notches 19 at spaced intervals along the top of rail 17 extend at an angle from the upper edge of the rear wall downward toward ledge 18 on the front wall to form an acute angle at the top of the rail as best illustrated in FIG. 2.

The angle of notches 19 depends somewhat on the particular configuration of clip 30 but in general, an angle of about 45 degrees plus or minus 10 degrees is within the operative range. Base 11 optionally includes side projections 20 and 21 which assist in holding the cartridge on a flat surface while removing clips therefrom.

Film 12 consists of paper, plastic, or other thin sheet material which is interposed between cover plate 13 and body 11 to hold the clips in position on rail 17. Film 12 is perforated or embossed to form a longitudinal line of weakness 22 extending down the center thereof and a series of crossing lines 23 extending across the major portion of the width thereof. The crossing lines are spaced to coincide with the spacing between notches 19 along the top of the rail.

Cover plate 13 includes access apertures 24 which are spaced directly over notches 19 to communicate with the clips in the assembled cartridge. As illustrated, apertures 24 are rectangular slots, square at one end and rounded at the other to provide visual orientation corresponding to the orientation of the clips contained in the cartridge.

FIG. 3 illustrates a typical clip 30 for use with the cartridge of the present invention. The clip includes head 31 at the end of one leg in the form of a hook member adapted to receive and hold end 32 of the other leg member when the clip is closed by rotating the legs together about integral hinge 33.

FIG. 4 is an end view from the left side of the cartridge of FIG. 1 illustrating the position of the clips on center rail 17. As illustrated, clip 30 is positioned on rail 17 in notch 19 with head 31 of the clip resting on ledge 18 of the rail. Leg 32 projects into space on the opposite side of the rail. Film 12 bears against the top of clip 30 to hold it in position on the rail. The angle of notch 19 corresponds to the angle formed by the clip when positioned as illustrated so that the surface of notch 19 bears on the inside surface of the leg of the clip to provide a stable support for the clip.

Clips are removed from the cartridge of FIG. 1 by inserting a forceps-type clip applier into the cartridge through apertures 24 in the cover plate as illustrated in FIG. 6. As the forceps enter the cartridge, film 12 is ruptured along lines 22 and 23 adjacent the point of entry. As the forceps continue into the cartridge, the film leaflets are pushed into the interior of the cartridge until the forceps engage the clip which is then readily removed from the cartridge as the forceps are withdrawn.

FIG. 5 is a top plan view of the cartridge of FIG. 1 after some clips have been removed from the first three positions. As illustrated, film 12 has been ruptured and displaced into the cartridge exposing rail 17 and giving ready visual indication that the clips have been removed from these positions. In the remaining six positions, film 12 remains intact giving visual indication that clips remain in the cartridge below these positions.

Turning now to FIGS. 7 and 8, there are illustrated variations of the cartridge of the present invention which do employ the film and cover members of the cartridge of FIG. 1. In FIG. 7, clips 30 are held in position on rail 17 by means of finger springs 40 and 41 extending from side walls 15 and 14 respectively. Foam pad 42 is used to support the free leg of clip 30 against the pressure of spring 41. When the appliers are inserted into the cartridge over the clip, springs 40 and 41 are displaced toward the side walls, and foam 42 is compressed to allow the forceps to fully engage and remove the clip.

FIG. 8 is a variation of the cartridge of FIG. 1 wherein only a single finger spring 43 extending from base 11 is used to hold clip 30 in position on rail 17. The free end of spring 43 has a reverse curve away from the center of the cartridge to facilitate the displacement of the spring by the forceps during removal of the clip. Spring 43 bears on clip 30 at a point intermediate head 31 and hinge 33 and with a force substantially at right angles to the plane of the leg of the clip in order to hold the clip securely against center rail 17.

The cartridges of FIGS. 7 and 8 may have an open top or be covered with a plate similar to cover plate 13 of FIG. 1. An open cartridge has the advantage of total visibility and accessibility and simplicity of construction. The covered cartridge has the advantage of guiding the forceps precisely over the clip and is the generally preferred configuration for the cartridges of this invention.

The cartridges of this invention are conveniently molded of plastic and discarded after the clips have been removed. The finger springs of FIGS. 7 and 8 may be metal or plastic. If a cover plate is utilized, it is also most conveniently a molded plastic piece. After loading the clips into the cartridge, the cover plate is fused to the body member in accordance with conventional plastic assembly techniques. The entire unit is then sterilized with, for example, ethylene oxide and packaged in a sterile enclosure until ready for use.

In the event the clips are formed of a moisture-sensitive absorbable material such as a polymer of lactide and/or glycolide, the assembled unit is desiccated and placed in a dry, hermetically sealed package to prevent degradation of the clips during storage. Where the clips are fabricated of a nonabsorbable material such as nylon, precautions to exclude all traces of moisture from the package are not necessary.

While the foregoing has described certain specific embodiments of the cartridge according to the present invention, other embodiments will readily be apparent to those skilled in the art. The essential element of the present invention resides in the configuration of the cartridge, particularly the center rail, for supporting plastic clips of the type illustrated in FIG. 3. In particular, the cartridges in accordance with the present invention utilize a center rail having a raised step to form a ledge along one side thereof to support the head of the clip and an upper surface angled away from the step to support the leg of the clip when positioned on the rail. The clip is thus firmly supported by one leg on the rail while the other leg extends freely into the space between the rail and the wall of the cartridge. This configuration allows the forceps-type clip applier to engage the clip by displacing the free leg of the clip while the supported leg remains firmly in position. The rail configuration also assures that all clips are oriented in the same direction and spaced uniformly along the length of the rail.

We claim:

1. A cartridge for holding a plurality of plastic ligating clips, each clip having one leg terminating in a hook-like head member adapted to engage and retain the free end of the other leg of the clip when the clip is closed by pivoting about an integral hinge section, comprising a body member having a base and two side walls forming an elongated channel a central rail extending from the base of said channel along the length thereof parallel to and spaced from said side walls said rail having a step on one side thereof forming a ledge extending along the length of said rail a plurality of uniformly spaced notches along the top of said rail angled toward said ledge and means for holding one leg of a clip in position on said rail with the head of the clip on said ledge and the leg of said clip resting on the angled surface of said notch.

2. The cartridge of claim 1 wherein said notches are angled at about 45 degrees.

3. The cartridge of claim 1 wherein the means for holding the clips on the rail comprise a finger spring bearing on the leg of the clip at a point intermediate the head and hinge of said clip.

4. The cartridge of claim 3 wherein the force of the spring is substantially at right angles to the plane of the leg of the clip.

5. The cartridge of claim 3 wherein the finger spring extends from the base of said cartridge.

6. The cartridge of claim 1 wherein the means for holding the clip on the rail comprise two finger springs extending from each wall of said cartridge body and bearing on the central portion of each leg of the clip.

7. The clip of claim 6 wherein the free leg of the clip is supported against the force of the finger spring by a foam pad.

8. The cartridge of claim 1 wherein the means for holding the clip on the rail comprise a film extending across the open side of the body member and in contact with the clip, whereby the clip is restrained between said film and said rail.

9. The cartridge of claim 8 wherein said film is secured to said cartridge body by means of a cover plate having a series of apertures in registry with the position of the clips on the rail in the cartridge.

10. The cartridge of claim 8 wherein said film is weakened along a line extending above the rail and along either side of the apertures in the cover plate.

11. A cartridge of claim 9 wherein the apertures in the cover plate are unsymmetrical and aligned with the orientation of the clips within the cartridge.

12. A cartridge for plastic ligating clips comprising a cartridge body and a plurality of clips removably mounted therein, each of said clips comprising two legs joined by an integral hinge, one of said legs terminating in a head comprising a hook member adapted to receive and hold the free end of the other leg when said clip is closed said cartridge body comprising a base and two side walls forming an elongated channel a central rail extending from the base of said channel along the length thereof parallel to and intermediate said side walls said rail being of a substantially rectangular shape having a step on one side thereof forming a ledge extending along the length of said rail and resulting in the upper portion of said rail being of a narrower width than the base portion a plurality of uniformly spaced notches along the top portion of said rail, said notches being angled toward said ledge a plurality of clips positioned on said rail with the head of each clip resting on said ledge and the leg of each clip resting on the angled surface of said notch and means for holding said clip in position on said rail.

13. The cartridge of claim 12 wherein said notches are angled at about 45 degrees.

14. The cartridge of claim 12 wherein the means for holding the clips on the rail comprise a finger spring bearing on the leg of the clip at the point intermediate the head and hinge of said clip.

15. The cartridge of claim 14 wherein the force of the spring is substantially at right angles to be the plane of the leg of the clip.

16. The cartridge of claim 14 wherein the finger spring extends from the base of said cartridge.

17. The cartridge of claim 12 wherein the means for holding the clip on the rail comprise two finger springs extending from each wall of said cartridge body and bearing on the central portion of each leg of the clip.

18. The clip of claim 17 wherein the free leg of the clip is supported against the force of the finger spring by a foam pad.

19. The cartridge of claim 12 wherein the means for holding the clip on the rail comprise a film extending across the open side of the body member and in contact with the clip, whereby the clip is restrained between said film and said rail.

20. The cartridge of claim 19 wherein said film is secured to said cartridge body by means of a cover plate having a series of apertures in registry with the position of the clips on the rail in the cartridge.

21. The cartridge of claim 19 wherein said film is weakened along a line extending above the rail and along either side of the apertures in the cover plate.

22. A cartridge of claim 20 wherein the apertures in the cover plate are unsymmetrical and aligned with the orientation of the clips within the cartridge.

* * * * *